(12) United States Patent
Bigorra Llosas et al.

(10) Patent No.: US 7,959,723 B2
(45) Date of Patent: Jun. 14, 2011

(54) USE OF BIOCIDE COMPOSITIONS FOR WOOD PRESERVATION

(75) Inventors: Joaquin Bigorra Llosas, Sabadell (ES); Rainer Höfer, Düsseldorf (DE); Bernd Fabry, Korschenbroich (DE); Jean-Pierre Molitor, Buthiers (FR); Stéphanie Merlet, Corbeil-Essonnes (FR); Ramon Valls, Barcelona (ES)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 12/677,013

(22) PCT Filed: Aug. 29, 2008

(86) PCT No.: PCT/EP2008/007066
§ 371 (c)(1),
(2), (4) Date: Mar. 8, 2010

(87) PCT Pub. No.: WO2009/030433
PCT Pub. Date: Mar. 12, 2009

(65) Prior Publication Data
US 2010/0251927 A1    Oct. 7, 2010

(30) Foreign Application Priority Data

Sep. 7, 2007   (EP) .................................. 07017537

(51) Int. Cl.
*A01N 43/653* (2006.01)
*A01N 25/02* (2006.01)
*A01P 3/00* (2006.01)
*B27K 3/34* (2006.01)
*B27K 3/16* (2006.01)
*B27K 3/38* (2006.01)

(52) U.S. Cl. .................. 106/18.32; 106/15.05; 427/297; 427/397; 514/740

(58) Field of Classification Search ............... 106/15.05, 106/18.32; 427/297, 397; 514/740
See application file for complete search history.

(56) References Cited

U.S. PATENT DOCUMENTS

| | | |
|---|---|---|
| 3,954,977 A | 5/1976 | Rife |
| 4,234,665 A | 11/1980 | Johnston |

FOREIGN PATENT DOCUMENTS

| | | |
|---|---|---|
| EP | 0453899 A1 | 10/1991 |
| EP | 0555186 A1 | 8/1993 |
| WO | 93/01801 A1 | 2/1993 |
| WO | 95/15685 A1 | 6/1995 |
| WO | 96/15885 A1 | 5/1996 |
| WO | 99/02037 A1 | 1/1999 |
| WO | 99/55505 A1 | 11/1999 |
| WO | 2007/092580 A2 | 8/2007 |

OTHER PUBLICATIONS

Zeitschrift fur Chemisch-Technische Industrie, die Technische Chemie und Spezialchemikalien Heinrich Becker, Seifen—Ole—Fette—Wachse, Sep. 1989, vol. 115, pp. 469-475.
Wo steht der Holzschutz heute?* H. Willeitner Holz als Roh- und Werkstoff 49 (1991), pp. 41-46.

*Primary Examiner* — Anthony J Green
(74) *Attorney, Agent, or Firm* — Fox Rothschild LLP

(57) ABSTRACT

The invention is directed to the use of compositions (a) biocides, and (b) dialkylamides, for wood protection.

18 Claims, No Drawings

USE OF BIOCIDE COMPOSITIONS FOR WOOD PRESERVATION

CROSS REFERENCE TO RELATED APPLICATIONS

This application is the National Phase entry of PCT/EP2008/007066, filed Aug. 29, 2008, which claims priority to EPO patent application number 07017537, filed Sep. 7, 2007, which are incorporated herein by reference in their entireties.

FIELD OF THE INVENTION

The present invention is related to the area of biocides and concerns the use of new biocide compositions comprising environmental friendly solvents for the preservation of woods.

BACKGROUND OF THE INVENTION

Wood and/or cellulose based products exposed in an outdoor environment are biodegradable, primarily through attack by microorganisms. As a result, they will decay, weaken in strength, and discolor. The microorganisms causing wood deterioration include brown rots such as *Postia placenta, Gloeophyllum trabeum* and *Coniophora puteana*, white rots such as *Irpex lacteus* and *Trametes versicolor*, dry rots such as *Serpula lacrymans* and *Meruliporia incrassata* and soft rots such as *Cephalosporium, Acremonium* and *Chaetomium*. Treatment and protection of wood has been practiced for almost as long as the use of wood itself. Some accounts reach back to the beginning of recorded history. For example the Bible in Genesis, 6:13-14 "And God said unto Noah . . . make thee an ark of gopher wood; rooms shall thou make in the ark, and shall pitch it within and without with pitch." There are also records of wood preservation reaching back to ancient Greece during Alexander the Great's rule, where bridge wood was soaked in olive oil. The Romans also protected their wood by brushing their ship hulls with tar. During the Industrial Revolution wood preservation became a corner stone of the wood processing industry. Inventors and scientists such as Bethell, Boucherie, Burnett and Kyan made historic developments in wood preservation, with the preservative solutions and processes.

For treating the sleepers of the Cologne-Minden railway, one of the first connections between Cologne via Düsseldorf through the Ruhr area, Julius Rütgers founded in 1849 the "Rütgers-werke, being the first impregnation company working with tar oil and carbolineum. Today the use of such compounds is rather limited due to its high content of polycyclic aromatics; nevertheless they are still applied for the preservation of railway sleepers and poles.

Detailed overviews covering the area of wood preservation are provided for example by H. Becker [Seifen Öle Fette Wachse, Vol. 115, 469ff (1989)], and H. Willeitner [Holz als Rohund Werkstoff, 49, 41ff (1991)]

Water is the most common solvent carrier in preservative formulations due to its availability and low cost. For example, between 1984 and 1996 the market for water-borne products has been doubled its volume. Water-borne systems do however have the drawback that they swell timber, leading to increased twisting, splitting and checking than alternatives. For these reason usually organic solvents, for example NMP, white spirit or fatty acid alkyl esters are used. These compounds do not swell the timber, however show various other disadvantages. In particular at least some of these compounds must be regarded as little environmental-friendly due to their toxic potential and high volatility so that they do not match the legal standards which have been introduced by various countries during the recent years. Others, like for example fatty acid alkyl esters can be regarded as ecologically safe, however their solvent power is sometimes poor so that high amounts of carrier are necessary to formulate a preservative composition that is stable over longer storage times and at higher temperatures.

In the context of the present invention reference is made to European patent EP 0453899 B1 (Bayer) disclosing the use of dimethylamides derived from saturated $C_6$-$C_{20}$ fatty acids as crystallisation inhibitors for azol derivatives which can be applied as fungicides. The patent neither mentions nor suggests the solvent properties of dialkylamides in general nor their use in wood preservation.

The object of the present invention has therefore to provide new compositions for wood or timber preservation avoiding the disadvantages of the state of the art as explained above. In particular the new compositions should exhibit an improved solvent power, comply with the high environmental safety standards and support the biocide activity of standard preservatives.

DETAILED DESCRIPTION OF PREFERRED EMBODIMENTS.

The present invention refers to the use of compositions comprising (a) biocides, and (b) dialkylamides for wood protection.

Surprisingly it has been observed that dialkylamides represent powerful solvents for the a broad spectra of biocides, more particularly wood or timber preservation agents, regardless whether they are water or oil borne. For example, the replacement of coco fatty acid methyl ester by the same amount of coco fatty acid dimethylamide makes it possible to double the content of triazole preservatives in a composition without separation even in case the mixtures are stored over 4 weeks at elevated temperatures. Due to its toxicological acceptance and low volatility compositions comprising dialkylamides as solvents also comply with the high environmental standards for wood preservation a lot of countries have introduced in the recent years. The present invention also encompasses the observation that dialkylamides contribute to the preservation properties of the biocides without showing biocide activity on their own.

Biocides

A biocide (component a) is a chemical substance capable of killing different forms of living organisms used in fields such as medicine, agriculture, forestry, and mosquito control. In the course of the present invention the phrase "biocide" is preferably used for wood, timber or lumber preservation agents Usually, timber or lumber that is treated with a preservative generally have it applied through vacuum and/or pressure treatment. The preservatives used to pressure-treat lumber are classified as pesticides. Treating lumber provides long-term resistance to organisms that cause deterioration. If it is applied correctly, it extends the productive life of lumber by five to ten times. If left untreated, wood that is exposed to moisture or soil for sustained periods of time will become weakened by various types of fungi, bacteria or insects. Chemical preservatives can be classified into three broad categories:

Water-soluble salts,
Oil-soluble preservatives, and
Light Organic Solvent Preservatives (LOSP).

Water-Soluble Preservatives

Chromated copper arsenate (CCA). Chromated copper arsenate (CCA) is an extremely common preservative originally developed in the 1930s at the Forest Research Institute in Dehra Dun, India. In CCA treatment, copper is the primary fungicide, arsenic is a secondary fungicide and an insecticide, and chromium is a fixative which also provides ultraviolet (UV) light resistance. Recognized for the greenish tint it imparts to lumber, CCA is a preservative that was extremely common for many decades, however it contained arsenic. In the last decade concerns were raised that the chemicals may leach from the wood into surrounding soil, resulting in concentrations higher than naturally occurring background levels. Therefore, today the use of CCA is restricted by environmental law.

Alkaline copper quaternary. Alkaline copper quaternary (ACQ) is a preservative made up of copper, a fungicide, and quaternary ammonium compound, an insecticide which also augments the fungicidal treatment. The U.S. began mandating the use of non-arsenic containing wood preservatives for virtually all residential use lumber in 2004, although the products are rather corrosive to common steel due to its high copper content.

Azoles. Suitable examples for active azoles are selected from the group consisting of azaconazole, bromuconazole, Cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, simeconazole, tebuconazole, tetraconazole, thiabendazole, triadimefon, triadimenol, triticonazole, uniconazole, uniconazole-P, 2-(2,4-difluorophenyl)-1-(1H-1,2,4-triazole-1-yl)-3-trimethylsilyl-2-prop-anol, amisulbrom, bitertanol, fluotrimazole, triazbutil, climbazole, clotrimazole, imazalil, oxpoconazole, prochloraz, triflumizole and combinations thereof.

Copper azoles. Copper azole preservative (denoted as CA-B under American Wood Preservers Association standards) is the other major copper based wood preservative that has come into wide use in the USA, Europe, Japan and Australia following restrictions on CCA. The Copper Azole preservative is based on alkaline amine copper complex similar to that in ACQ but incorporates organic triazoles such as tebuconazole or propiconazole as the co-biocide. General appearance of wood treated with copper azole preservative is similar to CCA and ACQ.

Other copper compounds. Additional examples for copper compounds also useful for wood or limber preservation are copper HDO (CuHDO), copper chromate, copper citrate, acid copper chromate and ammonium copper zinc arsenate (ACZA). The CuHDO treatment is an alternative to CCA, ACQ and CA used in Europe and in approval stages for United States and Canada. AZCA is generally used for marine applications.

Borate preservatives. Boric acid, oxides and salts (borates) are also effective wood preservatives and are supplied under numerous brand names throughout the world. Borate treated wood is of low toxicity to humans, and does not contain copper or other heavy metals. However unlike most other preservatives, borate compounds do not become fixed in the wood and can readily be leached out. Therefore they should not be used where they will be exposed to rain, water or ground contact. Recent interest in low toxicity lumber for residential use, along with new regulations restricting some wood preservation agents, has resulted in a resurgence of the use in borate treated wood for floor beams and internal structural members.

Sodium silicate-based preservatives. Sodium silicate is produced by fusing sodium with sand or heating both ingredients under pressure. It has been in use since the 1800s. It can be a deterrent against insect attack and possesses minor flame-resistant properties; however, it is easily washed out of wood by moisture, forming a flake-like layer on top of the wood. One company, Timber Treatment Technology, LLC, has found that infusing lumber with a chemical solution containing sodium silicate with a specified energy level applied yields wood that not only does not provide flake or layering on the wood, nor does it wash out as others have done in the past; and it provides processed lumber that received a class A fire classification. Their processed wood also paints and stains as new wood does. Other uses include fixing pigments in paintings and cloth printing, and for preserving eggs.

Oil-Soluble Preservatives

Coal-tar Creosotes and pentachlorophenol. Creosote is a tar-based preservative that has been commonly used for telephone poles and railroad ties. Creosote is one of the oldest wood preservatives, and was originally derived from a wood distillate. These days virtually all creosote is manufactured from the distillation of coal tar. It often collects inside chimneys and may cause a fire hazard. Creosote is regulated as a pesticide and is not usually sold to the general public. It is still used for railway sleepers and utility poles.

Linseed oil. In recent years in Australia and New Zealand, Linseed has been incorporated in preservative formulations as a solvent and water repellent to "envelope treat" timber. This involves just treating the outer 5 mm of the cross-section of a timber member with preservative, leaving the core-untreated. While not as effective as CCA or LOSP methods, envelope treatments are significantly cheaper as they use far less preservative. Major preservative manufacturers add a blue dye to envelope treatments. There is an on-going promotional campaign in Australia for this type of treatment. Linseed oil is used to preserve wood fences, log cabins, and wood furniture (such woods as willow, pine, oak, etc.) The function of linseed oil as a preservative is believed to be related to its action as a water repellent and drying agent rather than a direct biocide activity.

Light Organic Solvent Preservatives (LOSP)

This class of timber treatment use white spirit as the solvent carrier to deliver preservative compounds into timber. Synthetic pyrethroids are used as an insecticide, such as permethrin, bifenthrin or deltamethrin. In Australia and New Zealand, the most common formulations use permethrin as an insecticide, and propaconazole and/or tebuconazole as fungicides. While still using a chemical preservative, this formulation contains no heavy-metal compounds. With the introduction of strict volatile organic compound (VOC) laws in the European Union, LOSP have disadvantages due to the high cost and long process times associated with vapourrecovery systems. LOSP have been emulsified into water-based solvents. While this does significantly reduce VOC emissions, the timber swells during treatment, removing many of the advantages of LOSP formulations. Also Tung oil has been known about for hundreds of years in China, where it was used as a preservative for wood ships. The oil penetrates the wood, and then hardens to form an impermeable hydrophobic layer up to 5 mm into the wood. As a preservative it is effective for exterior work above and below ground, but the thin layer makes it less useful in practice. It is not available as a pressure treatment. Some manufacturers recommend tung oil as a stabiliser for CCA.

The preferred biocides are represented by species belonging to the group of azole derivatives as explained in more detail in EP 0553899 B1 cited above. As far as the nature of the azole derivatives is concerned the teaching of the patent is incorporated by reference. As particular useful biocides tebuconazole, fenbuconazole, epoxiconazole and their mixtures were identified.

Dialkylamides

According to the present invention dialkylamides (compound b) can be derived from derived from saturated or unsaturated, optionally hydroxy-substituted mono- di- or tricarboxylic acids. The preferred dialkylamides are dimethylamides or diethylamides. The various types suitable to function as green solvents and synergists for water-borne or oil-borne preservatives are explained in more detail as follows.

Dialkylamides Based on Monocarboxylic Acids

Dialkylamides based on monocarboxylic acids, particularly fatty acids follow the general formula (I),

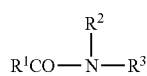
(I)

in which $R^1CO$ stands for an aliphatic or aromatic acyl radical having 6 to 22 carbon atoms, preferably 8 to 12 carbon atoms and 0 or 1 to 3 double bonds, and $R^2$ and $R^3$ independently from each other represent a $C_1$-$C_4$ alkyl or hydroxyalkyl radical. Typical examples are dialkylamides based on caproic acid, caprylic acid, 2-ethyl hexanoic acid, caprinic acid, lauric acid, myristic acid, palmitic acid, stearic acid, isostearic acid, oleic acid, (conjugated) linolic acid, linoleic acid, gadoleic acid, arachidonic acid, behenic acid, erucic acid, tall oil fatty acid, and their technical mixtures or benzoic acid. Examples for suitable alkyl groups are methyl, ethyl, propyl, i-propyl, n-butyl, i-butyl, and tert.-butyl.

Dialkylamides Based on Dicarboxylic Acids

In a second embodiment, said dialkylamides can be derived from dicarboxylic acids following general formula (II)

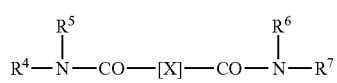
(II)

in which $R^4$, $R^5$, $R^6$ and $R^7$ independently from each other represent a $C_1$-$C_4$ alkyl or hydroxyalkyl radical and X stands for an alkylene group having 1 to 12 carbon atoms. Typical examples are the symmetrical or asymmetrical diamides based on maleic acid, fumaric acid or adipic acid. Examples for suitable alkyl groups are again methyl, ethyl, propyl, i-propyl, n-butyl, i-butyl, and tert.-butyl. In another preferred embodiment of the present invention, those dialkylamides are used which show similar alkyl groups, preferably methyl groups, since dimethylamides exhibit superior solvent properties. Therefore, the residues $R^4$ to $R^7$ in formulae (I) and (II) preferably represent methyl groups.

The species showing the best solvent properties can be found in the group comprising the $C_6$-$C_{12}$ fatty acid dimethylamides, such as, for example, capric acid dimethylamide or caprylic fatty acid dimethylamide which are especially preferred for the purpose of the present invention.

Dialkylamides Derived from Hydroxy Carboxylic Acids

In the alternative, dialkylamides according to the present invention can be derived from hydroxy-substituted mono-, di- or tricarboxylic acid. In case the carboxylic acid has two or three acid groups, the amide may be a mono-, di- or triamide or represent a statistical mixture. In a first embodiment of the present invention, dialkylamides follow the general formula (III),

in which $R^8CO$ stands for a hydroxysubstituted acyl radical having 1 to 22 carbon atoms, and $R^9$ and $R^{10}$ independently represent hydrogen or represent a $C_1$-$C_4$ alkyl or hydroxyalkyl radical. Typical examples are dialkylamides of lactic acid, ricinoleic acid or 12-hydroxy stearic acid. Other suitable dialkylamides can be derived from citric acid or tartaric acid or their mixtures. The preferred dialkylamides represent dimethylamides. The most preferred species exhibiting the best performance in dissolving or dispersing a wide number of different biocides over a long period and both at low and high temperatures is lactic acid dimethylamide.

Industrial Application

Wood Preservation Compositions

According to the present invention the preservation composition may comprise between about 0.1 and about 30, preferably about 1 to about 25% b.w. and more preferably about 5 to about 15% b.w. of a suitable biocide or biocide mixture. The remaining part to 100% b.w. shall be formed by dialkylamides. For specific purposes the solvent part of the composition may also comprise fatty acid alkyl esters or NMP up to a content of 50% b.w. The preservative concentration depends whether one wants to sell a ready-to-use formulation with low biocide content or a concentrate to be diluted for example with water. The final composition may also contain further auxiliary agents, like for example emulsifiers. A final embodiment of the present invention is therefore directed to the use of dialkylamides as "green" environmental-friendly solvents for biocides, in particular for wood preservation agents, preferably of the azole type.

Application of the Compositions

There are numerous non-pressure processes of treating wood which vary primarily in their procedure. It is possible to use the compositions according to the present invention in all of these processes. The most common of these treatments involve the application of the preservative by means of brushing or spraying, dipping, soaking, steeping or by means of hot and cold bath. There is also a variety of additional methods involving charring, applying preservatives in bored holes, diffusion processes and sap displacement.

Non-Pressure Processes

Brushing. Also brushing preservatives is a long-practiced method and often used in today's carpentry workshops. Through technology developments it is also possible to spray preservative over the surface of the timber. Some of the liquid is drawn into the wood as the result of capillary action, but this penetration is insignificant and not suitable for long-term weathering. By using the spray method, coal-tar creosote, oil-borne solutions and water-borne salts (to some extent) can also be applied. A thorough brush or spray treatment with coal-tar creosote can add 1 to 3 years to the lifespan of poles or posts. Two or more coats provide better protection than one, but the successive coats should not be applied until the prior coat has dried or soaked into the wood. The wood should be seasoned before treatment.

Dipping. Dipping consists of simply immersing the wood in a bath of creosote or other preservative for a few seconds or minutes. Similar penetrations to that of brushing and spraying processes are achieved. It has the advantage of minimizing hand labour. It requires more equipment and larger quantities of preservative and is not adequate for treating small lots of timber. Usually the dipping process is useful in the treatment of window sashes and doors. Treatment with Copper salt preservatives is no longer allowed with this method.

According to the so-called "steeping" process the wood is submerged in a tank of water-preservative mix, and allowed to soak for a longer period of time (several days to weeks). This process was developed in the 19$^{th}$ century by John Kyan. The depth and retention achieved depends on factors such as species, wood moisture, preservative and soak duration. The majority of the absorption takes place during the first two or three days, but will continue at a slower pace for an indefinite period. As a result, the longer the wood can be left in the solution, the better treatment it will receive. When treating seasoned timber, both the water and the preservative salt soak into the wood, making it necessary to season the wood a second time. Posts and poles can be treated directly on endangered areas, but should be treated at least 30 cm (1 ft) above the future ground level. The depth obtained during regular steeping periods varies from 5 mm to 10 mm (⅛ to ⅓ in.) up to 30 mm (1 in.) by sap pine. Due to the low absorption, solution strength should be somewhat stronger than that in pressure processes, around 5% for seasoned timber and 10% for green timber (because the concentration slowly decreases as the chemicals diffuse into the wood). The solution strength should be controlled continually and, if necessary, be corrected with the salt additive. After the timber is removed from the treatment tank, the chemical will continue to spread within the wood if it has sufficient moisture content. The wood should be weighed down and piled so that the solution can reach all surfaces. (Sawed materials stickers should be placed between every board layer.) This process finds minimal use despite its former popularity in continental Europe and Great Britain. A special embodiment of this process is called "kyanizing" named after John Howard Kyan, who developed this process in England in 1832, the wood in steeped a 0.67% mercuric chloride preservative solution.

Hot and Cold Bath process. According to this process developed by C. A. Seeley, seasoned wood is treated in successive baths of hot and cold preservatives. During the hot baths, the air expands in the timbers. When the timbers are changed to the cold bath (the preservative can also be changed) a partial vacuum is created within the lumen of the cells, causing the preservative to be drawn into the wood. Some penetration occurs during the hot baths, but most of it takes place during the cold baths. This cycle is repeated with a significant time reduction compared to other steeping processes. Each bath may last 4 to 8 hours or in some cases longer. The temperature of the preservative in the hot bath should be between 60 to 110° C. and 30 to 40° C. in the cold bath (depending on preservative and trees species). The average penetration depths achieved with this process ranges from 30 mm to 50 mm (1 to 12/3 in.). Both preservative oils and water-soluble salts can be used with this treatment. Due to the longer treatment periods, this method finds little use in the commercial wood preservation industry today.

Osmosis process. In the osmosis process, first developed in Germany, the preservative is applied to the surface of green wood in the form of a cream or paste. The wood is then stacked in solid piles, which are covered securely with waterproof tarp to prevent moisture loss. The treated wood is left covered for 30 days (up to 90 days), as the water-soluble portions of the preservative diffuse into the water of the green wood. The osmosis process is often used in the United States and Canada for the treatment of fence posts, as well as the subsequent treatment of ground-line areas for standing poles. But because of its intensive time and labour consumption it is not used on a large scale basis.

Pressure Processes

Pressure processes are those in which the treatment is carried out in closed cylinders with applied pressure and/or vacuum. These processes have a number of advantages over the non-pressure methods. In most cases, a deeper and more uniform penetration and a higher absorption of preservative is achieved. Another advantage is that the treating conditions can be controlled so that retention and penetration can be varied. These pressure processes can be adapted to large-scale production. The high initial costs for equipment and the energy costs are the biggest disadvantages. These treatment methods are used to protect ties, poles and structural timbers and find use throughout the world today. The various pressure processes that are used today differ in details, but the general method is in all cases the same. The treatment is carried out in cylinders. The timbers are loaded onto special tram cars, so called "buggies," and into the cylinder. These cylinders are then set under pressure often with the addition of higher temperature. As final treatment a vacuum is frequently produced to extract excess preservatives. These cycles can be repeated to achieve better penetration. LOSP treatments often use a vacuum impregnation process. This is possible because of the lower viscosity of the white-spirit carrier used.

Full-Cell Process. In the Full-cell process, the intent is to keep as much of the liquid absorbed into the wood during the pressure period as possible, thus leaving the maximum concentration of preservatives in the treated area. Usually, water solutions of preservative salts are employed with this process but it is also possible to impregnate wood with oil. The desired retention is achieved by changing the strength of the solution. Burnett patented this development in 1838 of Full-Cell Impregnation with water solutions. The patent covered the use of zinc chloride on water basis, also known as "Burnettizing". This process is still used today with some improvements.

Fluctation Process. Contrary to the "static" Full-Cell and Empty-Cell processes, the Fluctuation Process is a "dynamic" Process. By this process the pressure inside the impregnation cylinder changes between pressure and vacuum within a few seconds. There have been inconsistent claims that through this process it is possible to reverse the pit closure by Spruce. However the best results that have been achieved with this process by Spruce do not exceed a penetration deeper than 10 mm. Specialized equipment is necessary and therefore higher investment costs are incurred.

Boucherie-Process. Developed 1838 in France, this approach consisted of attaching a bag or container of preservative solution to a standing or a freshly cut tree with bark, branches, and leaves still attached, thereby injecting the liquid into the sap stream. Through transpiration of moisture from the leaves the preservative is drawn upward through the sapwood of the tree trunk. The modified Boucherie process consists of placing freshly cut, unpeeled timbers onto declining skids, with the stump slightly elevated, then fastening watertight covering caps or boring a number of holes into the ends, and inserting a solution of copper sulfate or other waterborne preservative into the caps or holes from an elevated container. Preservative oils tend to not penetrate satisfactorily by this method. The hydrostatic pressure of the liquid forces the preservative lengthwise into and through the sapwood, thus pushing the sap out of the other end of the timber. After a few days, the sapwood is completely impregnated; unfortunately little or no penetration takes place in the heartwood. Only green wood can be treated in this manner. This process has found considerable usage to impregnate poles and also larger trees in Europe and North America, and has experienced a revival of usage to impregnate bamboo in countries such as Costa Rica, Bangladesh, India and the state of Hawaii.

High Pressure Sap Displacement System. Developed in the Philippines, High pressure sap displacement system (HPSD) consists of a cylinder pressure cap made from a 3 mm thick mild steel plate secured with 8 sets of bolts, a 2-HP diesel engine, and a pressure regulator with 1.4-14 kg/m2 capacity. The cap is placed over the stump of a pole, tree or bamboo and the preservative is forced into the wood with pressure from the engine.

Incising process. First tested and patented by Kolossvary et al. in 1911 the Incising process consists of making shallow, slit-like holes in the surfaces of material to be treated, so that deeper and more uniform penetration of preventative may be obtained. The term "incising" or perforating comes from Latin incidere, a compound of in and caedere (to cut). This process can also be used to ensure a long durability of food through its packaging. The air exchange can be ensured with laser-incised holes within packaging that are so fine that moisture does not escape. Incisions made in sawed material usually are parallel with the grain of the wood. This process is common in North America (since the 1950s), where Douglas-Fir products and pole butts of various species are prepared before treatment. It is most useful for woods that are resistant to side penetration but allow preservative transport along the grain. In the region in which it is produced, it is common practice to incise all sawed Douglas fir 3 in. or more in thickness before treatment.

Microwaving. An alternative method of increasing the permeability of timber involves using microwave technology. Ongoing research in this area is being conducted by the Cooperative Research Centre at the University of Melbourne, Australia.

As far as the application of the compositions to the wood is concerned the invention also encompasses colours and paints comprising the new compositions.

EXAMPLES

Examples 1 and 2, Comparison Examples C1 and C2

Wood preservative concentrates was prepared by dissolving tebuconazole in various organic solvents. The compositions were stored in clear bottles over a period of 2 and 4 weeks respectively and at a temperature of 20 and 40 ° C. respectively. Visual observations of the compositions over the storage time are reported in the following Table 1. The symbols have the following meaning: (+) clear solution (#) solution cloudy (−) separation. Examples 1 and 2 are according to the invention, examples C1 and C2 are included for comparison. The examples clearly show that dialkylamides exhibit a higher solvent power in comparison with methyl esters and allow the formulation of concentrates with significantly higher storage stability. The dialkylamides exhibit a comparable performance to NMP, however, are by far less toxic.

The examples clearly show that dialkylamides exhibit a higher solvent power in comparison with methyl esters and allow the formulation of concentrates with significantly higher storage stability, and they are a good alternative to replace existing toxic solvents like NMP

TABLE 1

Wood preservative concentrates - storage stability

| Ex. | Solvent | Tebuconazole [g] | Visual analysis after 2 weeks 20° C. | Visual analysis after 2 weeks 40° C. | Visual analysis after 4 weeks 20° C. | Visual analysis after 4 weeks 40° C. |
|---|---|---|---|---|---|---|
| C1 | Caprylic acid methyl ester | 10 | + | + | + | + |
|  |  | 25 | + | # | # | − |
|  |  | 50 | # | − | − | − |
| C2 | N-Methyl pyrrolidone (NMP) | 10 | + | + | + | + |
|  |  | 25 | + | + | + | + |
|  |  | 50 | + | + | + | + |
| 1 | Capric acid dimethylamide | 10 | + | + | + | + |
|  |  | 25 | + | + | + | + |
|  |  | 50 | + | + | + | + |
| 2 | Lactic acid dimethylamide | 10 | + | + | + | + |
|  |  | 25 | + | + | + | + |
|  |  | 50 | + | + | + | + |

What is claimed is:

1. A method of protecting wood, comprising the step of treating wood with a composition comprising:
  (a) at least one biocide,
  (b) at least one dialkylamide, and
  (c) optionally, a cosolvent selected from the group consisting of fatty acid alkyl esters and N-methylpyrrolidone (NMP), wherein said dialkylamide is represented by formula (II),

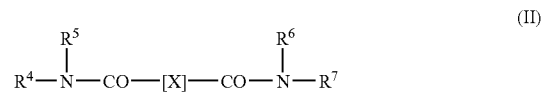

(II)

in which $R^4$, $R^5$, $R^6$ and $R^7$ independently represent $C_1$-$C_4$ alkyl or hydroxyalkyl, and X stands for an alkylene group having 1 to 12 carbon atoms, or by formula (III),

$R^8CO-NR^9R^{10}$ (III)

in which $R^8CO$ stands for a hydroxysubstituted acyl moiety having 1 to 22 carbon atoms and $R^9$ and $R^{10}$ independently represent $C_1$-$C_4$ alkyl or hydroxyalkyl.

2. The method of Claim 1 wherein said dialkylamide comprises a dimethylamide or diethylamide.

3. The method of Claim 1 wherein said composition comprises about 0.1 to about 30% by weight of said at least one biocide.

4. The method of Claim 1 wherein said composition is applied to the wood by pressure or non-pressure processes or in the form of stains or paints.

5. The method of claim 1, wherein said cosolvent (c) is present in 0-50% by weight.

6. A method of preparing wood or timber preserving compositions, comprising the step of dissolving at least one wood or timber preserving agent in at least one dialkylamide, wherein said dialkylamide is represented by formula (II),

(II)

in which $R^4$, $R^5$, $R^6$ and $R^7$ independently represent $C_1$-$C_4$ alkyl or hydroxyalkyl and X stands for an alkylene group having 1 to 12 carbon atoms, or by formula (III), $$R^8CO\text{—}NR^9R^{10} \quad (III)$$

in which $R^8CO$ stands for a hydroxysubstituted acyl moiety having 1 to 22 carbon atoms and $R^9$ and $R^{10}$ independently represent $C_1$-$C_4$ alkyl or hydroxyalkyl.

7. The method of claim 6 wherein said dialkylamide comprises a dimethylamide or diethylamide.

8. The method of claim 6 wherein said composition comprises about 0.1 to about 30% by weight of said at least one biocide.

9. The method of claim 6 wherein said composition is applied to the wood by pressure or non-pressure processes or in the form of stains or paints.

10. A method of protecting wood, comprising treating wood with a composition consisting of:

(a) one or more biocides, (b) one or more dialkylamides, and (c) 0-50% by weight of a cosolvent selected from the group consisting of fatty acid alkyl esters and N-methylpyrolidone (NMP), wherein said biocide is selected from the group consisting of tebuconazole, fenbuconazole and epoxiconazole.

11. The method of Claim 10 wherein said dialkylamide is represented by formula (I)

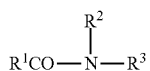
(I)

in which $R^1CO$ stands for an aliphatic or aromatic acyl moiety having 6 to 22 carbon atoms and 0 to 3 double bonds, and $R^2$ and $R^3$ independently represent $C_1$-$C_4$ alkyl or hydroxyalkyl.

12. The method of claim 10 wherein said dialkylamide comprises a dimethylamide or diethylamide.

13. The method of claim 10 wherein biocide component (a) is present in about 0.1 to about 30% by weight.

14. The method of claim 10 wherein said composition is applied to the wood by pressure or non-precesses or in the form of stains or paints.

15. A method of protecting wood, comprising treating wood with a composition consisting of:

(a) one or more biocides, (b) one or more dialkylamides, and (c) 0-50% by weight of a cosolvent selected from the group consisting of fatty acid alkyl esters and N-methylprrolidone (NMP), wherein said dialkylamide is represented by formula (II),

(II)

in which $R^4$, $R^5$, $R^6$ and $R^7$ independently represent $C_1$-$C_4$ alkyl or hydroxyalkyl, and X stands for an alkylene group having 1 to 12 carbon atoms, or by formula (III), $$R^8CO\text{—}NR^9R^{10} \quad (III)$$

in which $R^8CO$ stands for a hydroxysubstituted acyl moiety having 1 to 22 carbon atoms and $R^9$ and $R^{10}$ independently re resent $C_1$-$C_4$ alkyl or hydroxyalkyl. wood by pressure or non-pressure processes or in the form of stains or paints.

16. The method of claim 15 wherein said dialkylamide comprises a dimethylamide or diethylamide.

17. The method of claim 15 wherein biocide component (a) is present in about 0.1 to about 30% by weight.

18. The method of claim 15 wherein said composition is applied to the wood by pressure or non-pressure processes or in the form of stains or paints.

* * * * *